(12) United States Patent
Decoodt et al.

(10) Patent No.: US 8,123,952 B2
(45) Date of Patent: Feb. 28, 2012

(54) PROCESS AND DEVICE FOR SIMULATED MOVING BED SEPARATION WITH A MODULATED BY-PASS FLUID FLOW

(75) Inventors: Xavier Decoodt, Carrieres S/Seine (FR); Gerard Hotier, Rueil Maimaison (FR); Philibert Leflaive, Mions (FR); Damien Leinekugel Le Cocq, Lyons (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 0 days.

(21) Appl. No.: 13/059,773

(22) PCT Filed: Jul. 29, 2009

(86) PCT No.: PCT/FR2009/000946
§ 371 (c)(1),
(2), (4) Date: May 2, 2011

(87) PCT Pub. No.: WO2010/020715
PCT Pub. Date: Feb. 25, 2010

(65) Prior Publication Data
US 2011/0201865 A1 Aug. 18, 2011

(30) Foreign Application Priority Data
Aug. 19, 2008 (FR) ...................... 08 04637

(51) Int. Cl.
*B01D 15/08* (2006.01)
(52) U.S. Cl. ..... 210/659; 210/635; 210/656; 210/198.2; 585/825; 585/828
(58) Field of Classification Search .................. 210/635, 210/656, 659, 662, 198.2; 585/825, 828
See application file for complete search history.

(56) References Cited

U.S. PATENT DOCUMENTS 5,912,395 A 6/1999 Noe
5,972,224 A * 10/1999 Hotier et al. .................. 210/659
(Continued)

OTHER PUBLICATIONS

International Search Report of PCT/FR2009/000946 (Nov. 11, 2009).

*Primary Examiner* — Ernest G Therkorn
(74) *Attorney, Agent, or Firm* — Millen, White, Zelano & Branigan, P.C.

(57) ABSTRACT

A process for separating a feed F by simulated moving bed adsorption in a SMB device comprises at least one zone 1 for desorption of the compounds produced in the extract, a zone 2 for desorption of the compounds produced in the raffinate, a zone 3 for adsorption of the compounds produced in the extract, a zone 4 located between the raffinate withdrawal and the desorbant supply, the device comprising external by-pass lines $L_{i/i+1}$ directly connecting two successive plates $P_i$ and $P_{i+1}$;

in which the degree of opening of means for restricting the flushing flow rate of the by-pass lines $L_{i/i+1}$ are sequentially modified such that:

1) in an operational zone where there is at least one closed by-pass line, a super-synchronicity of the flushing flow rate is established in all of the by-pass lines which are not closed belonging to the zone under consideration, said super-synchronicity being defined by the following formula:

$$S = a + b(nf/nt)$$

in which the constant a is a constant in the range −5 to 5 and b is a constant in the range 40 to 100;

2) if there is no closed by-pass line in the zone under consideration (in other words if all of the by-pass lines of the zone are open), then a flow is established in all of the flushing lines of said zone which corresponds to the synchronicity plus or minus 8%.

4 Claims, 6 Drawing Sheets

U.S. PATENT DOCUMENTS

| | | | |
|---|---|---|---|
| 6,110,364 A * | 8/2000 | Hotier et al. | 210/198.2 |
| 6,537,451 B1 * | 3/2003 | Hotier | 210/198.2 |
| 6,797,175 B2 * | 9/2004 | Hotier | 210/659 |
| 8,049,055 B2 * | 11/2011 | Decoodt et al. | 585/828 |
| 2005/0269268 A1 | 12/2005 | Hotier | |
| 2010/0048973 A1 * | 2/2010 | Decoodt et al. | 585/822 |
| 2010/0258505 A1 * | 10/2010 | Decoodt et al. | 210/661 |
| 2011/0201865 A1 * | 8/2011 | Decoodt et al. | 585/822 |

* cited by examiner

PROCESS AND DEVICE FOR SIMULATED MOVING BED SEPARATION WITH A MODULATED BY-PASS FLUID FLOW

REFERENCE TO RELATED APPLICATIONS

This application is a 371 of PCT/FR09/00946 filed Jul. 29, 2009.

The following is an examiner's statement of reasons for allowance: U.S. Pat. No. 6,110,364 and U.S. Pat. No. 6,797,175 are considered to be the closest art because they disclose related processes. The case has been allowed because the recited combination of steps would not have been obvious from U.S. Pat. No. 6,110,364 and U.S. Pat. No. 6,797,175. Ser. No. 13/025,316 and Ser. No. 12/757,101 have been considered from a double patenting perspective. However, the claims of Ser. No. 13/025,316 and Ser. No. 12/757,101 are considered to be patentable over the instant claims.

FIELD OF THE INVENTION

The invention relates to the field of separation of natural or chemical products, which may be difficult to separate by distillation. A family of processes and associated devices is used which are known as simulated moving bed processes or separation devices, either in simulated counter current mode or in simulated co-current mode, which will hereinafter be designated by the generic term "SMB".

Particular but non-exclusive examples of the fields concerned are:
 The separation of normal paraffins from branched paraffins, naphthenes and aromatics;
 olefin/paraffin separation;
 the separation of para-xylene from other C8 aromatic isomers;
 the separation of meta-xylene from other C8 aromatic isomers;
 the separation of ethylbenzene from other C8 aromatic isomers.

Apart from the refinery and petrochemicals complex, there are a number of other applications; examples of these which can be cited include glucose/fructose separation, the separation of cresol positional isomers, optical isomer separation, etc.

PRIOR ART

SMB separation is well known in the art. As a general rule, a column operating in simulated moving bed mode comprises at least three zones, and possibly four or five, each of said zones being constituted by a certain number of successive beds, and each zone being defined by its position comprised between a supply point and a withdrawal point. Typically, a SMB column is supplied by at least one feed F to be fractionated and a desorbant D (sometimes termed the eluent), and at least one raffinate R and extract E are withdrawn from said column.

The supply and withdrawal points are modified over time, typically being offset in the same direction by a value corresponding to one bed.

By definition, each of the operational zones is designated by a number:
 zone 1=zone for desorption of compounds from the extract, comprised between the injection of the desorbant D and withdrawal of the extract E;
 zone 2=zone for desorption of compounds from the raffinate, comprised between the extract E withdrawal and injection of the feed F to be fractionated;
 zone 3=zone for adsorption of compounds from the extract, comprised between the feed injection and the raffinate R withdrawal;
 and preferably, a zone 4 located between the raffinate withdrawal and the desorbant injection.

The prior art describes in detail various devices and processes which can carry out simulated moving bed separation of feeds.

The following patents in particular can be cited: U.S. Pat. No. 2,985,589, U.S. Pat. No. 3,214,247, U.S. Pat. No. 3,268,605, U.S. Pat. No. 3,592,612, U.S. Pat. No. 4,614,204, U.S. Pat. No. 4,378,292, U.S. Pat. No. 5,200,075, U.S. Pat. No. 5,316,821. Those patents also describe the operation of a SMB in detail.

SMB devices typically comprise at least one column (usually two) divided into a plurality of successive beds A, of adsorbant, said beds being separated by plates $P_i$, each plate $P_i$ comprising one, two or four chambers, meaning that sequential operations of supplying feed or injecting desorbant and extracting raffinate or extract can be carried out.

A single chamber may carry out the 4 operations, but the present invention concerns columns with 2 chambers per plate. Many solutions are possible when using two chambers, each possibly being used for injection or withdrawal of one or more streams. As an example, a first chamber may carry out feed or desorption injection operations, and the other chamber carries out the operations of raffinate or extract withdrawal. Another possible case consists of using one chamber for injecting feed and withdrawing raffinate, the other handling injection of desorbant and withdrawal of extract. These two examples are not limiting; other uses of the two chambers are possible.

The control means for distributing and extracting fluids from a SMB are typically one of the two major following types of technology:
 either, for each plate, a plurality of controlled on-off valves to supply or withdraw fluids, said valves typically being located in the immediate vicinity of the corresponding plate. Each plate P, typically comprises at least 4 two-way valves, with on-off control, to respectively carry out supply of fluids F and D and withdrawal of fluids E and R;
 or a multi-way rotary valve for supply or withdrawal of fluids over the set of plates.

The present invention is in the context of SMB units using a plurality of valves to ensure supply and withdrawal of the various fluids.

Each of the plates $P_i$ typically comprises a plurality of distributer-mixer-extracter panels termed "DME plates" supplied via distribution/extraction lines or systems. The plates may be of any type and of any geometry. They are generally divided into panels, corresponding to adjacent sectors of the cross-section of the column, for example panels with angular sectors such as those shown in U.S. Pat. No. 6,537,451, FIG. 8, or panels with parallel sectors such as those described in U.S. Pat. No. 6,797,175.

Preferably, the separation column of the invention comprises DME plates of the parallel sector and dissymmetrical supply type.

Distribution over each of the beds requires the principal flow from the preceding bed to be collected, the possibility of injecting therein a supplemental or secondary fluid while mixing said two fluids as completely as possible, or the possibility of removing a portion of the collected fluid, extracting it to send it out of the device and also of re-distributing a fluid over the next bed.

A generic problem with all SMB devices is that of minimizing the pollution generated by the liquid in the various zones of the circuits for supply and withdrawal of fluids from the plates, during modification of the supply and withdrawal points during the operation of the SMB.

In fact, when, during the operational sequence, a line, chamber or zone for supplying a plate $P_i$ is no longer flushed by a fluid of the process, it becomes a dead zone in which the liquid stagnates, and is only moved again when another process fluid moves through it. Because of the operation of the SMB, it is then a process fluid which in general is different from the fluid stagnating in the line under consideration.

Mixing, or circulation over a short time interval of fluids with compositions which are substantially different, introduces perturbations into the concentration profile of the zone under consideration compared with the ideal operation where compositional discontinuities are to be avoided.

Another problem lies in possible recirculation between the various zones of a single plate, and more generally in the whole of the distribution/extraction system of a single plate, because of very small pressure differences between the various zones of the plate, which again indicates a disturbance with respect to ideal operation.

In order to overcome these problems linked to recirculation and dead zones, various solutions are known in the prior art:

a) flushing of the distribution/extraction system of a given plate using a desorbant or the desired product in a relatively pure state has already been proposed. This technique can in fact prevent pollution of the desired product during extraction thereof. However, since the flushing liquid has a composition which is very different from the liquid it displaces, this introduced discontinuities in the composition which are prejudicial to the ideal operation. This first flushing variation typically effects flushes of short duration with a high concentration gradient. These short duration flushes are short precisely in order to limit the effects of compositional discontinuities.

b) Another solution consists, as described in U.S. Pat. No. 5,972,224 and U.S. Pat. No. 6,110,364, in passing a majority of the principal flow into the column and a minority thereof (typically 1% to 20% of the principal flow) outside via external by-pass lines between successive plates. This flushing of the distribution/extraction system at a plate by a flow deriving from the upper plate is typically carried out continuously, such that the lines and zones of the distribution/extraction system are no longer "dead" but are constantly flushed.

Such a system with continuous flushing via by-pass lines is shown in FIG. 2 of patent FR-2 772 634. The by-pass lines generally have a small diameter and comprise a small diameter valve which reduces the cost of the system.

According to the disclosure of U.S. Pat. No. 5,972,224 and U.S. Pat. No. 6,110,364, the distribution/extraction system of a given plate is flushed with liquid with a composition which is very close to that of the displaced liquid (liquid present in the distribution system or circulating at the plate). Thus, mixing of fluids with different compositions is minimized and compositional discontinuities are reduced.

To this end, U.S. Pat. No. 5,972,224 and U.S. Pat. No. 6,110,364 recommend using flushing flow rates in the by-passes such that the transit rate in each by-pass is substantially the same as the advance rate of the concentration gradient in the principal flow of the SMB. This is then termed "synchronous" flushing or "synchronous flow rate" flushing. Thus, flushing of the various lines and volumes is carried out by a fluid with a composition which is substantially identical to that of the liquid therein, and the liquid moving in a by-pass is re-introduced at a point where the composition of the principal flow is substantially identical.

Flushing is thus synchronous over a long period for a small or zero concentration gradient.

According to the disclosure of that patent, flushing is termed "synchronous" when the flush flow rate $QS_{i/i+1}$ deriving from a plate $P_i$ to the next plate $P_{i+1}$ is equal to V/ST, in which V is the cumulative volume of the distribution systems of the plates $P_i$ (i.e. $V_i$) and $P_{i+1}$ (i.e. $V_{i+1}$) and of the volume of the by-pass line between these two plates (i.e. $VL_{i/i+1}$) and ST is the switch time for the SMB between two successive switches of the supply/extractions.

Thus, we have:

"Synchronous flow rate"=$QS_{i/i+1}$=$(V_i+V_{i+1}+VL_{i/i+1})$/ST, where:

$QS_{i/i+1}$=flush flow rate from plate $P_n$ to the adjacent plate (typically lower) $P_{i+1}$;

$V_i$=volume of distribution/extraction system of departing plate $P_i$;

$V_{i+1}$=volume of distribution/extraction system of arriving plate $P_{i+1}$;

$VL_{i/i+1}$=volume of by-pass line between $P_i$ and $P_{i+1}$;

ST=switch time.

Synchronous flushing is typically carried out by flushing at a controlled flow rate, adapted to each of the zones, of 50% to 150% of the synchronous flow rate in those zones, and ideally 100% of the synchronous flow rate. The flow rates in the by-pass lines of the 4 SMB zones are controlled by regulating means in each by-pass line.

As an example, the skilled person could use a flow rate of 90% of the synchronous flow rate in all of these zones, or 110% or even any other value for the synchronous flow rate which is close to 100%. However, when regulating means exist, the skilled person, following the disclosure of the patent cited above, will naturally elect to control the flow rates in the 4 zones which correspond exactly to the synchronous flow rate (100% of the synchronous flow rate).

One example of a SMB separation device of enormous industrial importance concerns the separation of C8 aromatic cuts with a view to producing para-xylene of commercial purity, typically of at least 99.7% by weight purity, and a raffinate which is rich in ethylbenzene, ortho-xylene and meta-xylene.

The two implementations cited above can achieve the aim of commercial purity. However, the Applicant has been able to show that while the disclosure of "synchronous flushing" of U.S. Pat. No. 5,972,224 and U.S. Pat. No. 6,110,364 provide a certain improvement over the prior art, it is still possible, surprisingly, to further improve the function and performances of simulated moving bed separation process by refining the rules defining the various flow rates of the by-pass lines.

BRIEF DESCRIPTION OF THE FIGURES

FIG. 1 shows a succession of 3 beds, $P_{i-1}$, $P_i$, $P_{i+1}$, which form part of a simulated moving bed column (SMB). The effluent withdrawal lines (raffinate or extract) are located upstream of the isolation valve of the by-pass line. The supply lines (for feed or desorbant) are located downstream of the isolation valve.

Zone 1 is represented by the curve with diamonds;
Zone 2 is represented by the curve with squares;
Zone 3 is represented by the curve with triangles;
Zone 4 is represented by the curve with circles.

FIG. 4 shows a succession of 3 beds, $P_{i-1}$, $P_i$, $P_{i+1}$, forming part of a simulated moving bed column (SMB). The effluent withdrawal lines (raffinate or extract) are located downstream of the isolation valve of the by-pass line. The supply lines (for feed or desorbant) are located upstream of the isolation valve.

Zone 1 is represented by the curve with diamonds;
Zone 2 is represented by the curve with squares;
Zone 3 is represented by the curve with triangles;
Zone 4 is represented by the curve with circles.

BRIEF DESCRIPTION OF THE INVENTION

The aim of the invention is to improve the performance of a simulated moving bed separation process over the disclosure in U.S. Pat. No. 5,972,224 and U.S. Pat. No. 6,110,364.

The invention also concerns an improved device for simulated moving bed separation using a plurality of controlled on-off 2 way valves for supplying and extracting SMB process fluids, by carrying out long duration flushing with a small or zero concentration gradient.

It has surprisingly been discovered that the ideal function of the by-pass lines does not correspond to a strictly synchronous flow rate over all of the operational zones of the SMB, but to a flow rate which differs depending on the zone of the SMB and which can in some cases represent a super-synchronicity which may or may not be substantial.

The term "super-synchronicity" means a value exceeding the value corresponding to synchronicity by at least 10%, and which is expressed as a percentage above said synchronicity. More precisely, said super-synchronicity is defined by the formula:

super-synchronicity(%)=100×[actual flow rate in by-pass line under consideration/synchronicity flow rate)−1]

More precisely, the present invention defines, for each zone of the SMB unit, a by-pass flow rate range comprising a certain degree of super-synchronicity which is specific to the zone under consideration.

This results in a complex optimum of the set of the by-pass flow rates, which depends both on the zone of the SMB under consideration and, as will be seen in the detailed description below, on the number of closed by-pass lines in said zone. This technical problem is completely absent from the prior art disclosure and constitutes a substantial advance in knowledge and skill in the field of SMB type processes.

Thus, the present invention concerns a process for simulated moving bed (SMB) separation of a feed F in a SMB device having at least one column, said column being composed of a plurality of beds of adsorbant separated by plates $P_i$ each comprising a distribution/extraction system, in which process the feed F and a desorbant D are supplied, and at least one extract E and at least one raffinate R are withdrawn, the supply and withdrawal points being offset over time by a value corresponding to one bed of adsorbant, with a switch time ST, and determining a plurality of operational zones of the SMB, in particular the following 4 principal zones:

a zone 1 for desorption of the compounds of the extract, comprised between the supply of the desorbant D and withdrawal of the extract E;

a zone 2 for desorption of raffinate compounds, comprised between the withdrawal of the extract E and the supply of the feed F;

a zone 3 for adsorption of the compounds of the extract, comprised between the supply of the feed and the withdrawal of the raffinate R;

a zone 4 located between the withdrawal of the raffinate R and the supply of the desorbant D;

the device further comprising external by-pass lines $L_{i/i+1}$ joining two successive plates $P_i$, $P_{i+1}$ directly, allowing said plates to be flushed, in which each of the by-pass lines $L_{i/i+1}$ comprises automated means for regulating the flushing flow rate, the degree of opening of said regulating means being defined by the following two rules:

1) in an operational zone where there is at least one closed by-pass line, a super-synchronicity of the flushing flow rate is established in all of the by-pass lines belonging to the zone under consideration, said super-synchronicity being defined by the following formula:

$$S=a+b(nf/nt)$$

in which a is a constant in the range −5 to 5, b is a constant in the range 40 to 100, which is multiplied by the ratio of the number of closed by-pass lines (nf) over the total number of by-pass lines (nt) of the zone under consideration;

2) if there is no closed by-pass line in the zone under consideration (in other words if all of the by-pass lines of the zone are open), then a flow is established in all of the flushing lines of said zone which corresponds to the synchronicity plus or minus 8%;

the synchronicity flow rate being defined as $(V_i+V_{i+1}+VL_{i/i+1})/ST$, in which expression $V_i$ denotes the volume of the distribution/extraction system of the departing plate $P_i$;

$V_{i+1}$ denotes the volume of the distribution/extraction system of the arriving plate $P_{i+1}$;

$VL_{i/i+1}$ denotes the volume of the by-pass line between $P_i$ and $P_{i+1}$;

and ST denotes the switch time.

The present invention also concerns a method for regulating the flushing flow rates for each zone constituting the SMB column which can be defined as follows:

1) the optimum synchronicity over a given zone is obtained by fixing the synchronicity at 100% for the set of by-pass lines which are not closed of the other zones;

2) and the optimum synchronicity obtained in the preceding step is attributed to each zone.

Finally, the process of the present invention is more particularly applicable to the separation of para-xylene or meta-xylene in a mixture of C8 aromatic hydrocarbons. Clearly, these two examples of applications are in no way limiting and other applications are possible, in particular in the field of separating normal and iso-paraffins or normal and iso-olefins.

DETAILED DESCRIPTION OF THE INVENTION

In order to improve the separation performances which can be produced by SMB techniques, the invention proposes a process for simulated moving bed (SMB) separation of a feed F in a SMB device having at least one column, said column being composed of a plurality of beds of adsorbant separated by plates $P_i$ each comprising a distribution/extraction system, in which process the feed F and a desorbant D are supplied, and at least one extract E and at least one raffinate R are withdrawn, the supply and withdrawal points being offset over time by a value corresponding to one bed of adsorbant, with a switch time ST, and determining a plurality of operational zones of the SMB, in particular the following 4 principal zones:

- a zone 1 for desorption of the compounds of the extract, comprised between the supply of the desorbant D and withdrawal of the extract E;
- a zone 2 for desorption of raffinate compounds, comprised between the withdrawal of the extract E and the supply of the feed F;
- a zone 3 for adsorption of the compounds of the extract, comprised between the supply of the feed and the withdrawal of the raffinate R;
- a zone 4 located between the withdrawal of the raffinate R and the supply of the desorbant D;

the device further comprising external by-pass lines $L_{i/i+1}$ joining two successive plates $P_i$, $P_{i+1}$ directly, allowing said plates to be flushed,
in which each of the by-pass lines $L_{i/i+1}$ comprises automated means for regulating the flushing flow rate.

The external by-pass line $L_{i/i+1}$ joining two successive plates $P_i$, $P_{i+1}$ directly is said to belong to a zone when the bed between the plates $P_i$ and $P_{i+1}$ belongs to said zone. A by-pass zone is said to be closed when the flow rate in this by-pass line is zero. This closure may be carried out using any technical means which can cancel the flow rate in the by-pass line, such as an on-off valve, a flow rate adjusting valve or a non-return valve.

The degree of opening of said regulating means is defined by the following two rules:
1) in an operational zone where there is at least one closed by-pass line, a super-synchronicity of the flushing flow rate is established in all of the by-pass lines which are not closed belonging to the zone under consideration, said super-synchronicity being in the range 10% to 100%;
2) if there is no closed by-pass line in the zone under consideration (in other words if all of the by-pass lines of the zone are open), then a flow is established in all of the by-pass lines of said zone which corresponds to the synchronicity plus or minus 8%, preferably plus or minus 5%;
the synchronicity flow rate being defined as $(V_i+V_{i+1}+VL_{i/i+1})/ST$, in which expression $V_i$ denotes the volume of the distribution/extraction system of the departing plate $P_i$;
$V_{i+1}$ denotes the volume of the distribution/extraction system of the arriving plate $P_{i+1}$;
$VL_{i/i+1}$ denotes the volume of the by-pass line between $P_i$ and $P_{i+1}$;
and ST denotes the switch time.

According to the above rule, it will be understood that the flushing flow rate of the by-pass lines in a given operational zone is essentially linked to the presence or otherwise of at least one closed by-pass line in said zone.

More precisely, the super-synchronicity S of the by-pass lines which are not closed in a zone where at least one closed by-pass line exists is defined by the ratio of the number of closed by-pass lines (nf) in the zone under consideration over the total number of by-pass lines in the zone (nt), i.e. over the number of beds in the zone under consideration.

The super-synchronicity S is defined as a percentage using the following formula:

$$S=a+b(nf/nt)$$

in which:
 a is a constant in the range −5 to 5;
 b is a constant in the range 40 to 100 multiplied by the ratio between the number of closed by-pass lines (nf) over the total number of by-pass lines (nt) of the zone under consideration.

An intense experimental study has shown that the coefficient b may be linked to the total number of beds in the unit (Nt) by the relationship:

$$b=(1320/\text{total number of beds in SMB unit}).$$

There may be several reasons for closing a by-pass line in a given zone. In particular, when a fluid (feed or desorbant) is injected into a plate $P_i$, an injection line is used. This line is connected to a by-pass line connected to said plate, i.e. either the by-pass line $L_{i/i+1}$ or the by-pass line $L_{i/i+1}$. Regardless which by-pass line is connected to the injection line used, it is then necessary to close said line using an on-off valve, a flow rate adjusting valve or a non return valve or any other technique which can cancel the flow rate to ensure that the injected fluid flows properly towards the plate $P_i$.

In the same manner, when an effluent (extract or raffinate) is withdrawn from a plate $P_i$, a withdrawal line is used. This withdrawal line is connected to a by-pass line connected to said plate, i.e. either the by-pass line $L_{i-1/i}$ or the by-pass line $L_{i/i+1}$.

Regardless which by-pass line is connected to the withdrawal line used, it is then necessary to close said line using an on-off valve, a flow rate adjusting valve or a non return valve or any other technical means which can cancel the flow rate to ensure that the fluid is properly withdrawn from the plate $P_i$.

The by-pass line to be closed for injection or withdrawal depends in particular on the position of the injection and withdrawal lines with respect to the by-pass line closing device.

The position of an element (plate, bed, valve, etc) described as being "downstream" of another element is defined with respect to the advancing direction of the points for withdrawal and introduction during the switching sequences.

As an example, in the case in which the lines for withdrawing effluents (raffinate or extract) are located upstream of the by-pass line closing device (or put more simply, "upstream of the by-pass line valve"), and where the supply lines (for feed or desorbant) are located downstream of the isolation valve:
 when a fluid (feed or desorbant) is injected into the plate $P_i$, an injection line connected to the by-pass line $L_{i-1/i}$ is used. It is thus necessary to close the isolation valve of the by-pass line $L_{i-1/i}$ in order to ensure that the injected fluid flows properly towards the plate $P_i$;
 when an effluent (extract or raffinate) is withdrawn from the plate $P_i$, a withdrawal line is used which is connected to the by-pass line $L_{i/i+1}$. It is then necessary to close the isolation valve of the by-pass line $L_{i/i+1}$.

Closing a by-pass line for each injection and each withdrawal involves closing a minimum of 4 by-pass lines permanently. Other by-pass lines may also be closed for other reasons.

EXAMPLES

The invention will be better understood from the following examples.

Example 1

A SMB unit was considered to be constituted by 24 beds, with a length of 1.1 m and an internal diameter of 3.5 m with a feed injection, a desorbant injection (which may also be termed the eluent or solvent), an extract withdrawal and a raffinate withdrawal. The plates had two mixing chambers, one being an injection box (feed and desorbant), the other being a withdrawal box (extract and raffinate).

The total volume $(V_i+V_{i+1}+VL_{i/i+1})$, where $VL_{i/i+1}$ is the volume of the by-pass line of plate $P_i$ to plate $P_{i+1}$ and where $V_i$ is the volume of the distribution/extraction system of plate $P_i$, represented 3% of the volume of the bed comprised between the plate $P_i$ and the plate $P_{i+1}$.

The effluent (raffinate or extract) withdrawal lines were located upstream of the isolation valve of the by-pass line (or more simply "upstream of the by-pass line valve").

Figure 1:
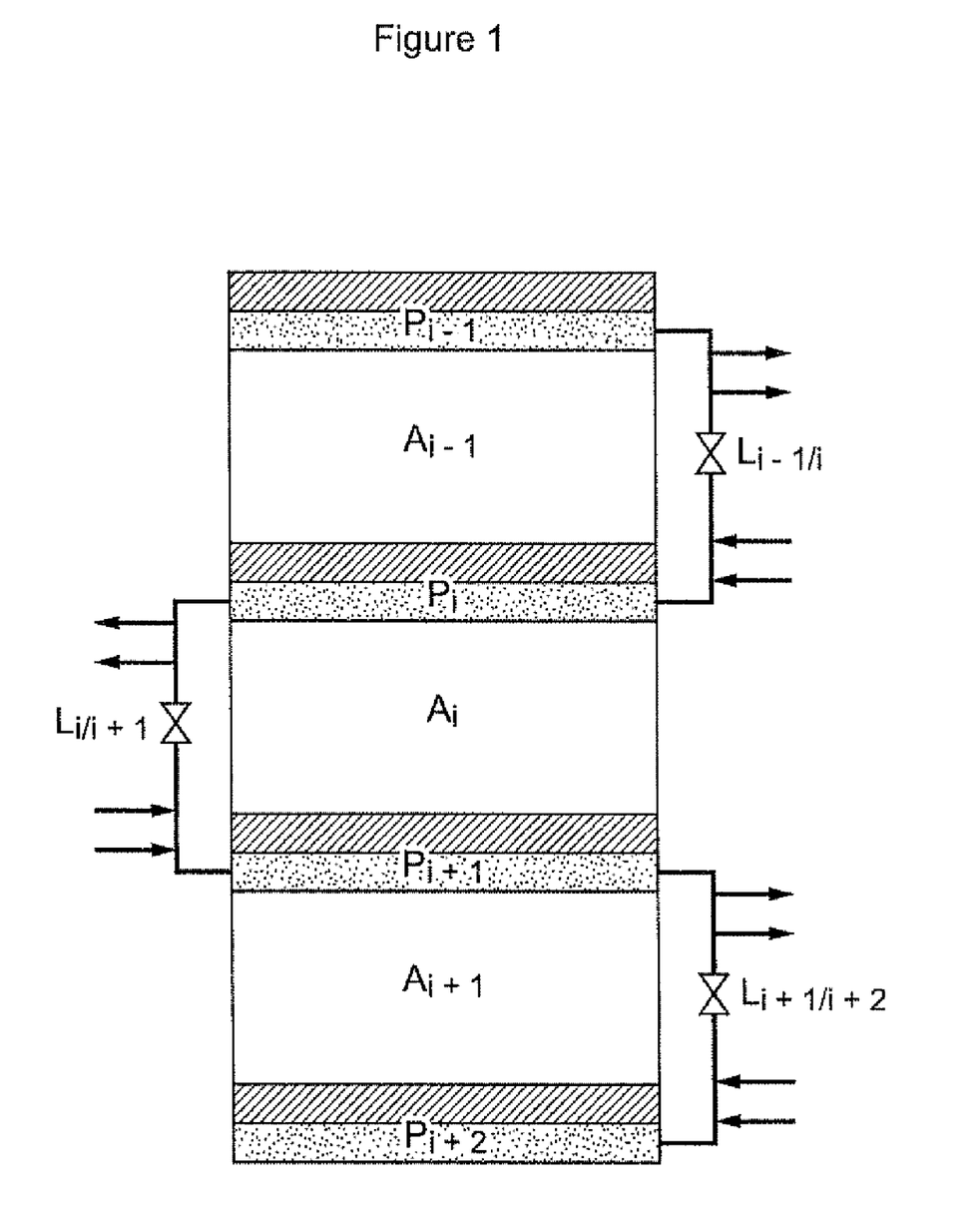

The supply lines (for feed or desorbant) were located downstream of the isolation valve (FIG. 1).

When a fluid (feed or desorbant) was injected into the plate $P_i$, an injection line was used which was connected to the by-pass line $L_{i-1/i}$. It was then necessary to close the isolation valve of the by-pass line $L_{i-1/i}$ to ensure that the injected fluid flowed properly towards the plate $P_i$.

Figure 2A:
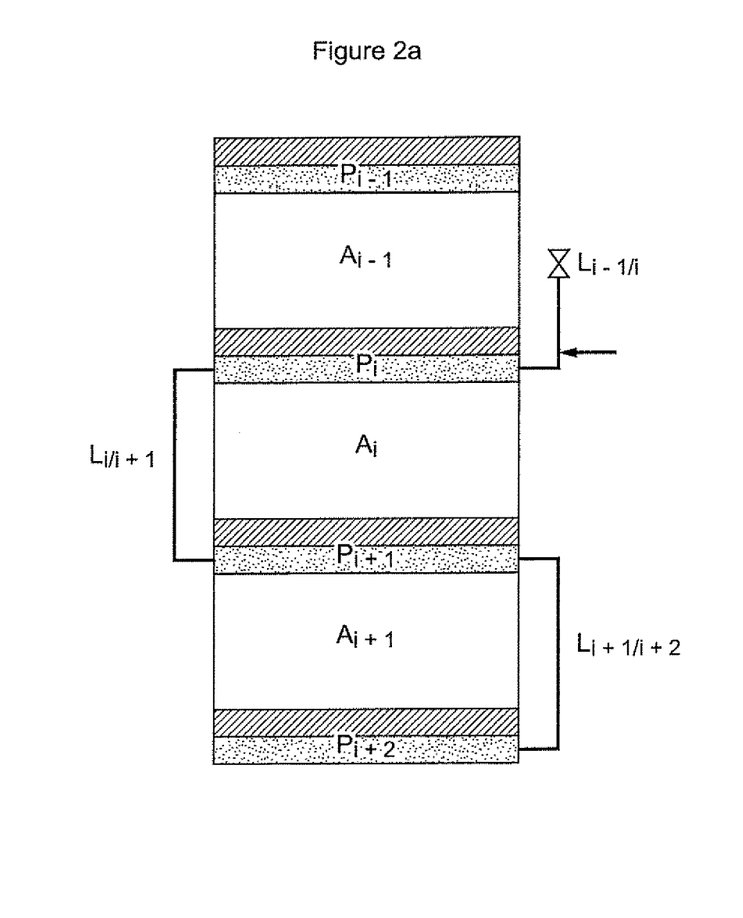
FIG. 2a shows an injection situation.
Figure 2B:
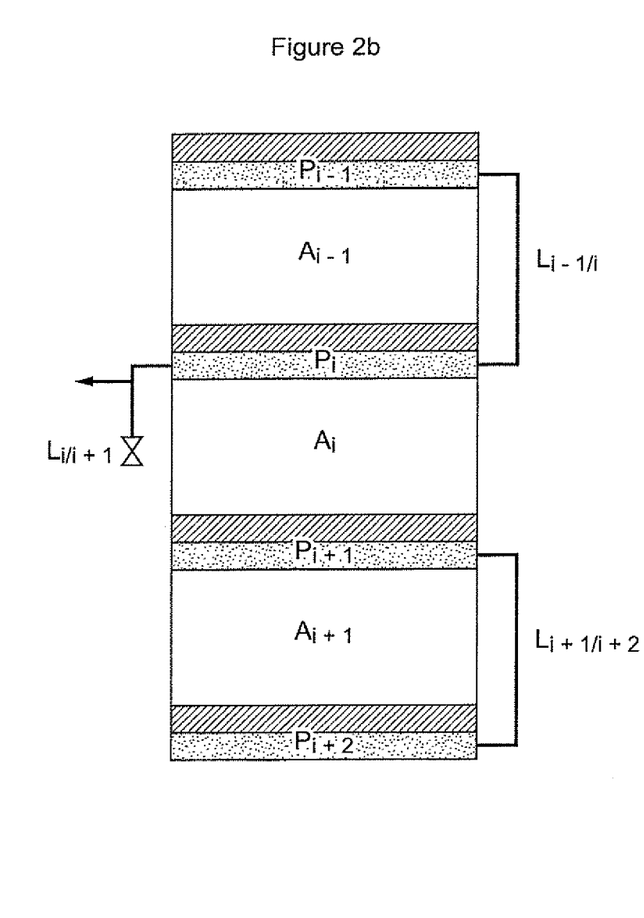
FIG. 2b shows a withdrawal situation in a configuration of the column of FIG. 1.

When an effluent (extract or raffinate) was withdrawn from the plate $P_i$, a withdrawal line was used which was connected to the by-pass line $L_{i/i+1}$. It was then necessary to close the isolation valve of the by-pass line $L_{i/i+1}$ (FIG. 2).

The result was that using this type of by-pass line resulted in:
- closure of two by-pass lines in zone 2 (withdrawal of extract via a line connected to the by-pass line of the first bed of the zone and injection of the feed via a line connected to the by-pass line of the last bed of the zone);
- closure of two by-pass lines in zone 4 (withdrawal of raffinate via a line connected to the by-pass line of the first bed of the zone and injection of desorbant via a line connected to the by-pass line of the last bed of the zone).

The beds were distributed in accordance with the configuration 5/9/7/3, i.e. the distribution of the beds was as follows:
- 5 beds in zone 1;
- 9 beds in zone 2;
- 7 beds in zone 3;
- 3 beds in zone 4.

The adsorbant used was a BaX type zeolite and the eluent used was para-diethylbenzene. The temperature was 175° C. and the pressure was 15 bars.

The feed was composed of 20% para-xylene, 24% ortho-xylene, 51% meta-xylene and 5% ethylbenzene. The switch time used was 70.8 seconds The liquid flow rates for injection of feed and desorbant were as follows:
- 6.81 m$^3$·min$^{-1}$ for the feed;
- 7.48 m$^3$·min$^{-1}$ for the desorbant;

i.e. a solvent ratio, S/F, of 1.1.

When the prior art synchronicity was adjusted to 100% for all of the open by-pass lines, simulation produced a para-xylene purity of 99.76% and a para-xylene yield of 95.80%.

The variation in the SMB performance, measured in terms of the PX yield for a fixed desorbant flow rate, feed flow rate, para-xylene purity produced and switch time, as a function of the synchronicity of all of the by-pass lines which were not closed of a zone, was calculated for each of the zones, retaining a synchronicity of 100% for the set of by-pass lines of the other zones which were not closed.

Figure 3:
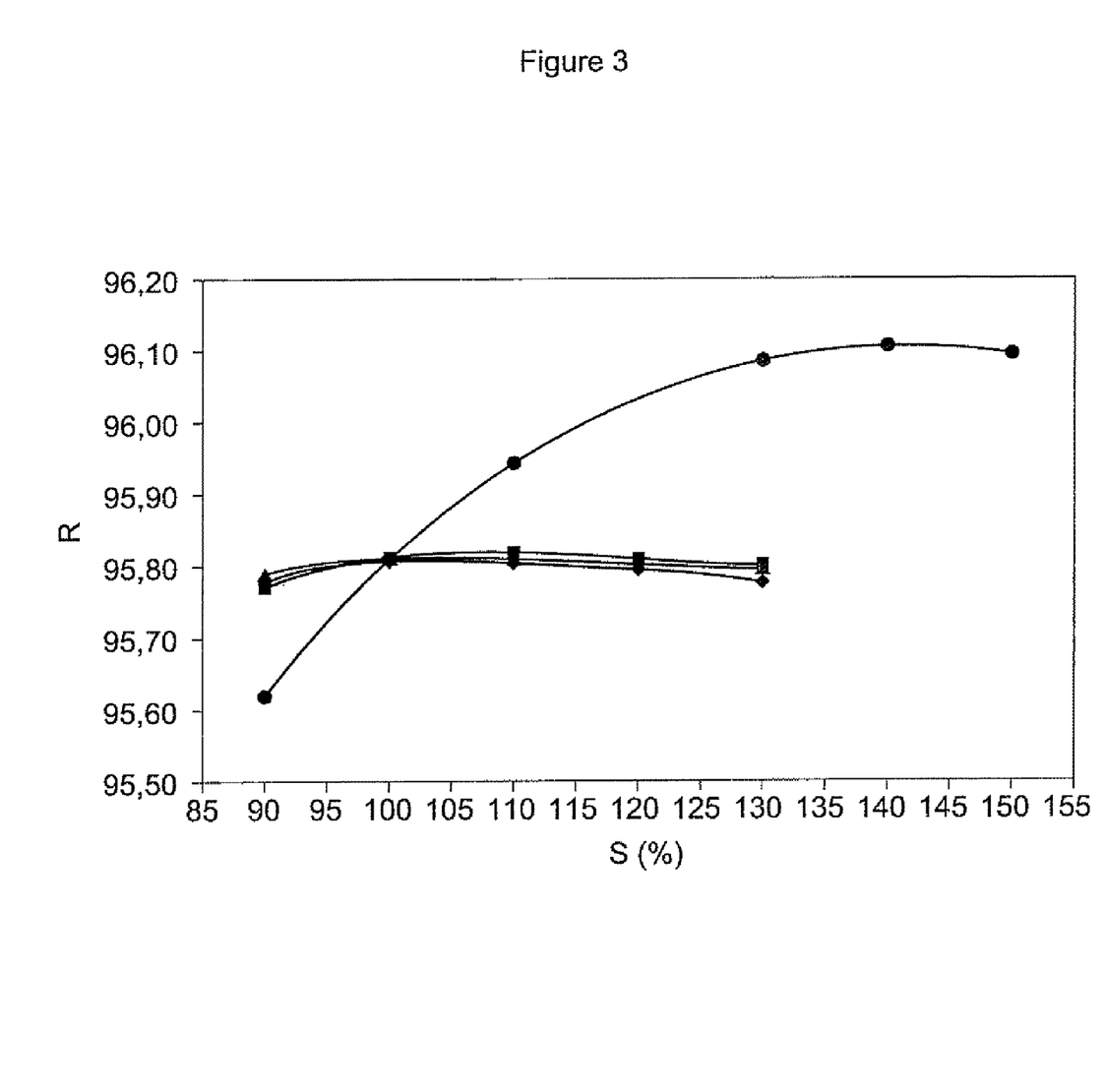
FIG. 3 shows the variations in performance of the SMB, measured in terms of yield (R) of PX, for a fixed flow rate of desorbant, flow rate of feed, purity of the para-xylene produced and switching time, as a function of the synchronicity (S) of all of the by-pass lines which are not closed for each of the zones which are not closed, retaining a synchronicity of 100% for the set of the by-pass lines of the other zones.

This variation in performance of the SMB is illustrated in FIG. 3 for each of the various zones. The PX yield is the ratio between the quantity of PX withdrawn from the extract and the quantity of PX injected.

- Zone 1 is represented by the curve with diamonds;
- Zone 2 is represented by the curve with squares;
- Zone 3 is represented by the curve with triangles;
- Zone 4 is represented by the curve with circles.

The yields at optimum synchronicity obtained for each zone at iso-purity, -feed flow rate, -switch time and -solvent ratio, are given in the table below.

|  | Optimum synchronicity | Yield |
|---|---|---|
| Zone 1 | 102% | 95.81% |
| Zone 2 | 110% | 95.82% |
| Zone 3 | 105% | 95.81% |
| Zone 4 | 140% | 96.10% |

After obtaining the optimum zone by zone, the four optimum synchronicity values were imposed simultaneously, namely 102% in zone 1, 110% in zone 2, 105% in zone 3 and 140% in zone 4.

At iso-purity, -feed flow rate, -switch time and -solvent ratio, a yield of 96.12% was obtained, which was higher than the yields obtained by adjusting the synchronicity for just one zone.

Clearly, using differentiated zone-dependent synchronicity results in a substantially improved yield over the prior art.

The optimum super-synchronicity for the set of zones may be defined by the following equation:

$$S=a+b(nf/nt) \text{ where } a=2.1, \text{ and } b=1320/24=55.$$

Example 2

We shall now consider a SMB unit constituted by 15 beds, with a length of 1.1 m and an internal diameter of 3.5 m with a feed injection, a desorbant injection (which may also be termed the eluent or solvent), an extract withdrawal and a raffinate withdrawal.

The plates had two mixing chambers, one being an injection box (feed and desorbant), the other being a withdrawal box (extract and raffinate).

The total volume $(V_i+V_{i+1}+VL_{i/i+i})$, where $VL_{i/i+1}$ was the volume of the by-pass line of plate $P_i$ to plate $P_{i+1}$ and where $V_i$ was the volume of the distribution/extraction system of plate $P_i$, represented 3% of the volume of the bed comprised between the plate $P_i$ and the plate $P_{i+1}$.

Figure 4:
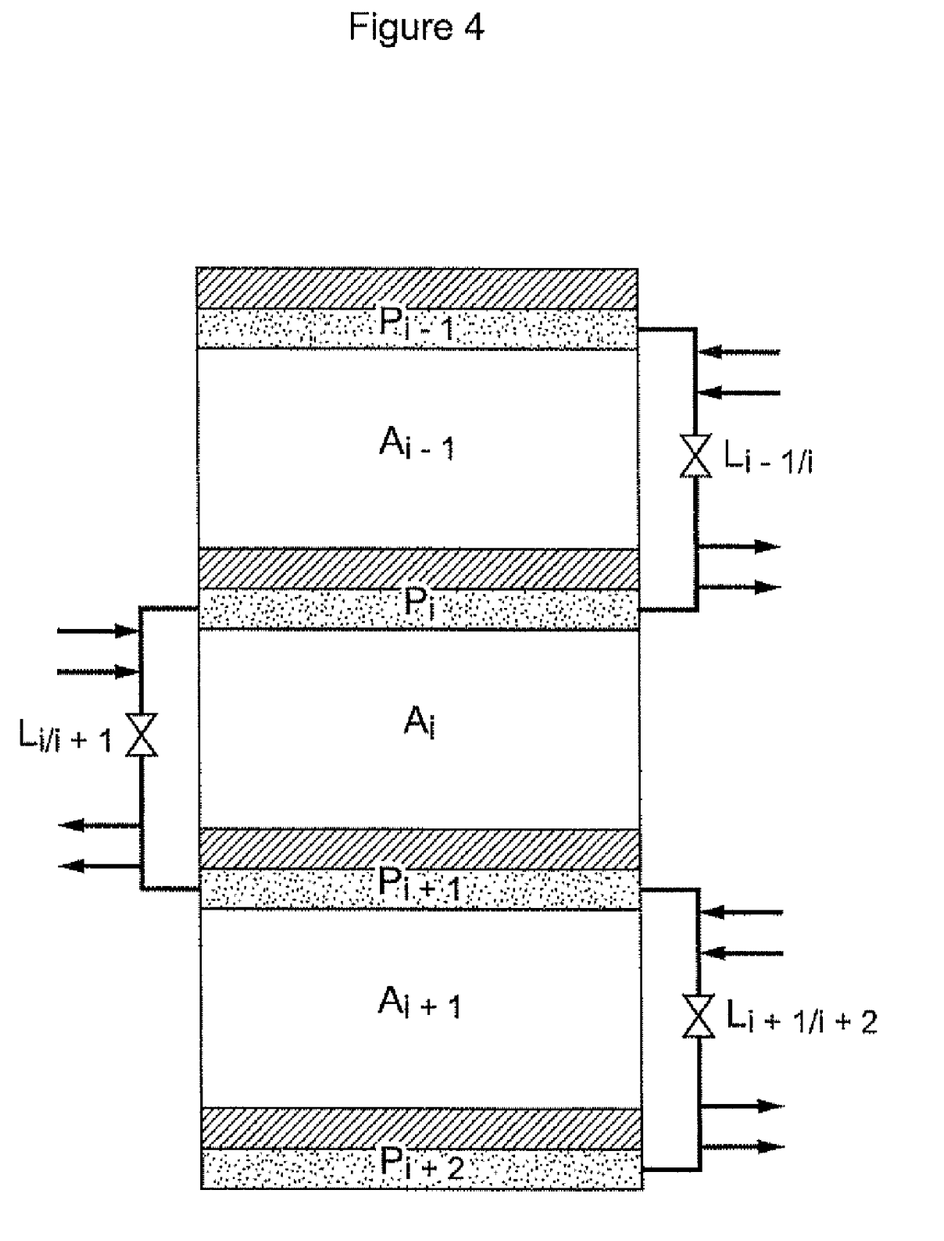

The effluent (raffinate or extract) withdrawal lines were now located downstream of the isolation valve of the by-pass line valve, and the injection points (for feed or desorbant) were located upstream of the isolation valve (FIG. 4).

When a fluid (feed or desorbant) was injected into the plate $P_i$, an injection line was used which was connected to the by-pass line $L_{i/i+1}$. It was then necessary to close the isolation valve of the by-pass line $L_{i/i+1}$ to ensure that the injected fluid flows properly towards the plate $P_i$.

Figure 5A:
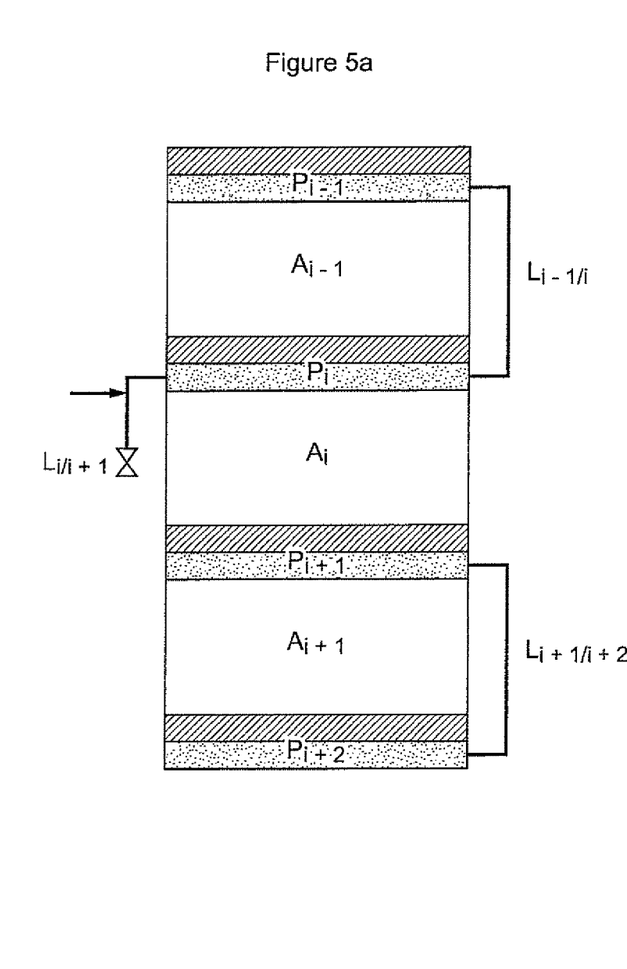
FIG. 5a shows an injection situation.
Figure 5B:
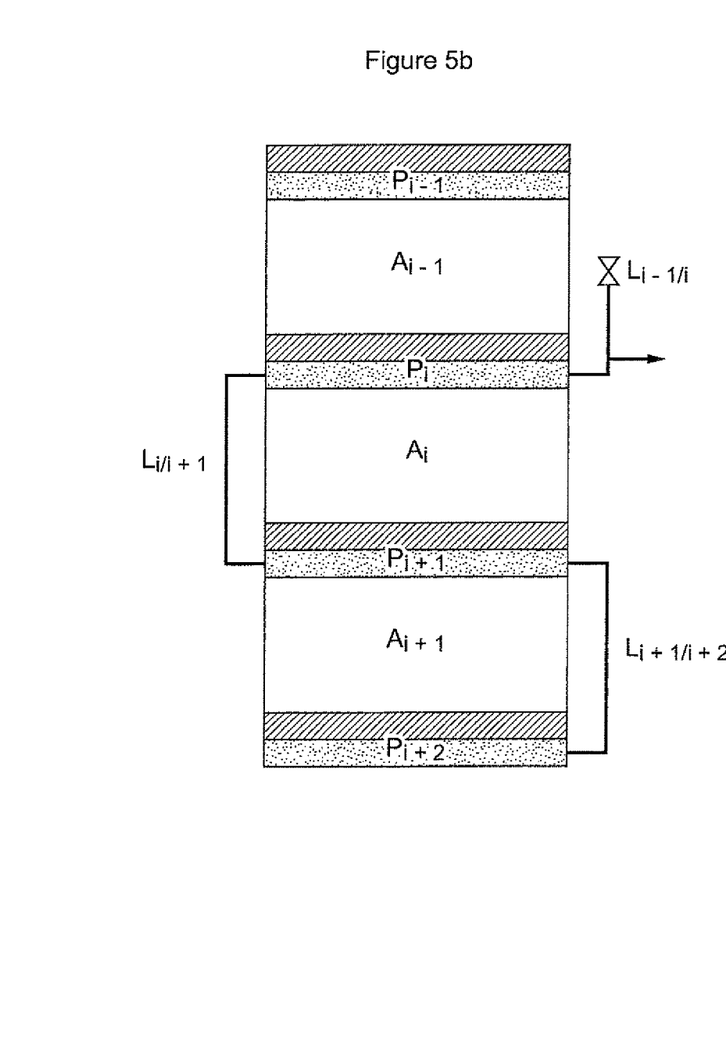
FIG. 5b shows a withdrawal situation in a configuration of the column according to FIG. 4.

When an effluent (extract or raffinate) was withdrawn from the plate $P_i$, a withdrawal line was used which was connected to the by-pass line $L_{i-1/i}$. It was then necessary to close the isolation valve of the by-pass line $L_{i-1/i}$ (FIG. 5).

The result was that using this type of by-pass line resulted in:
  closure of two by-pass lines in zone 1 (injection of desorbant via a line connected to the by-pass line of the first bed of the zone and withdrawal of extract via a line connected to the by-pass line of the last bed of the zone);
  closure of two by-pass lines in zone 3 (injection of feed via a line connected to the by-pass line of the first bed of the zone and withdrawal of raffinate via a line connected to the by-pass line of the last bed of the zone).

The beds were distributed in accordance with the configuration 3/6/4/2, i.e. the distribution of the beds was as follows:
  3 beds in zone 1;
  6 beds in zone 2;
  4 beds in zone 3;
  2 beds in zone 4.

The adsorbant used was a BaX type zeolite and the eluent used was para-diethylbenzene. The temperature was 175° C. and the pressure was 15 bars.

The feed was composed of 20% of para-xylene, 24% of ortho-xylene, 51% of meta-xylene and 5% of ethylbenzene. The switch time used was 113.28 seconds The liquid flow rates for injection of feed and desorbant were as follows:
  4.25 m$^3$·min$^{-1}$ for the feed;
  4.68 m$^3$·min$^{-1}$ for the desorbant;
i.e. a solvent ratio, S/F, of 1.1.

When the prior art synchronicity was adjusted to 100% for all of the open by-pass lines, simulation produced a para-xylene purity of 99.76% and a para-xylene yield of 91.46%.

The variation in the SMB performance, measured in terms of the PX yield for a fixed desorbant flow rate, feed flow rate, para-xylene purity produced and switch time, as a function of the synchronicity of all of the by-pass lines which were not closed of a zone, was calculated for each of the zones, retaining a synchronicity of 100% for the set of by-pass lines of the other zones which were not closed.

Figure 6:
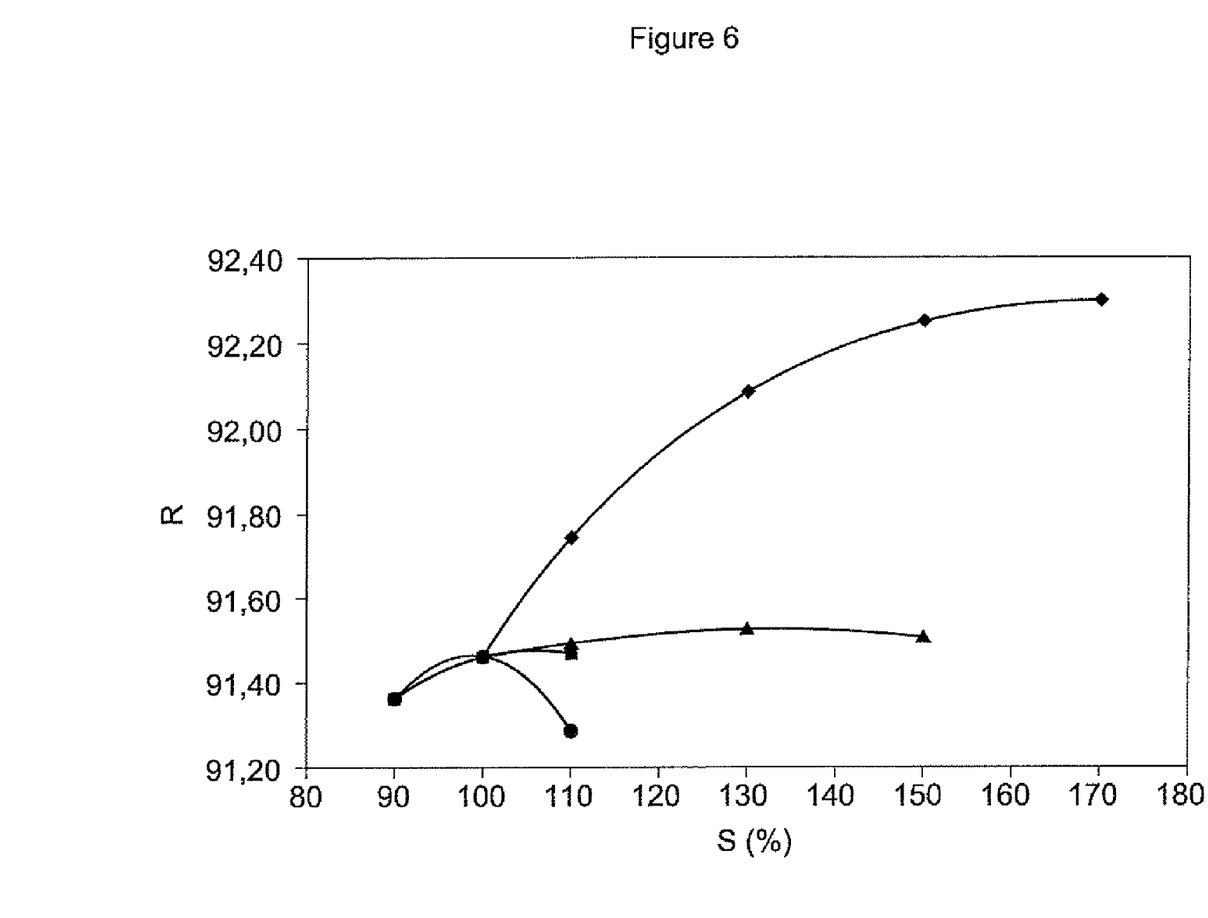
FIG. 6 shows the variations in SMB performance, measured in terms of yield (R) of PX for a fixed flow rate of desorbant, flow rate of feed, purity of the para-xylene produced and switching time, as a function of the synchronicity (S) of all of the by-pass lines which are not closed for each of the zones, retaining a synchronicity of 100% for the set of by-pass lines of the other zones which are not closed.

This variation in performance of the SMB is illustrated in FIG. 6 for each of the various zones.
  Zone 1 is represented by the curve with diamonds;
  Zone 2 is represented by the curve with squares;
  Zone 3 is represented by the curve with triangles;
  Zone 4 is represented by the curve with circles.

The PX yield is the ratio between the quantity of PX withdrawn in the extract and the quantity of PX injected.

The yields at optimum synchronicity obtained for each zone at iso-purity, -feed flow rate, -switch time and -solvent ratio are given in the table below.

|  | Optimum synchronicity | Yield |
| --- | --- | --- |
| Zone 1 | 170% | 92.31% |
| Zone 2 | 105% | 91.47% |
| Zone 3 | 133% | 91.53% |
| Zone 4 | 100% | 91.46% |

After obtaining the optimum zone by zone, the four optimum synchronicity values were imposed simultaneously, namely 170% in zone 1, 105% in zone 2, 133% in zone 3 and 100% in zone 4.

At iso-purity, -feed flow rate, -switch time and -solvent ratio, a yield of 92.34% was obtained, which was higher than the yields obtained by adjusting the synchronicity for just one zone.

Clearly, using differentiated zone-dependent synchronicity results in a substantially improved yield over the prior art.

The optimum super-synchronicity for the set of zones may be defined by the following equation:

$$S=a+b(nf/nt) \text{ where } a=0.9, \text{ and } b=1320/15=88.$$

The invention claimed is:
1. A process for simulated moving bed (SMB) separation of a feed F in a SMB device having at least one column, said column being composed of a plurality of beds of adsorbant separated by plates $P_i$ each comprising a distribution/extraction system, in which process the feed F and a desorbant D are supplied, and at least one extract E and at least one raffinate R are withdrawn, the supply and withdrawal points being offset over time by a value corresponding to one bed of adsorbant, with a switch time ST, and determining a plurality of operational zones of the SMB, in particular the following 4 principal zones:
  a zone 1 for desorption of the compounds produced in the extract, comprised between the supply of the desorbant D and withdrawal of the extract E;
  a zone 2 for desorption of the compounds produced in the raffinate, comprised between the withdrawal of the extract E and the supply of the feed F;
  a zone 3 for adsorption of the compounds produced in the extract, comprised between the supply of the feed and the withdrawal of the raffinate R;
  a zone 4 located between the withdrawal of the raffinate R and the supply of the desorbant D;
  the device further comprising external by-pass lines $L_{i/i+1}$ joining two successive plates $P_i$, $P_{i+1}$ directly, allowing said plates to be flushed, in which each of the by-pass lines $L_{i/i+1}$ comprises automated means for regulating the flushing flow rate, the degree of opening of said regulating means being defined by the following two rules:
1) in an operational zone where there is at least one closed by-pass line, a super-synchronicity of the flushing flow rate is established in all of the by-pass lines which are not closed belonging to the zone under consideration, said super-synchronicity being defined by the following formula:

$$S=a+b(nf/nt)$$

in which the constant a is a constant in the range −5 to 5 and b is a constant in the range 40 to 100, which is multiplied by the ratio of the number of closed by-pass lines (nf) over the total number of by-pass lines (nt) of the zone under consideration;
2) if there is no closed by-pass line in the zone under consideration (in other words if all of the by-pass lines of the zone are open), then a flow is established in all of the flushing lines of said zone which corresponds to the synchronicity plus or minus 8%;
  the synchronicity flow rate being defined as $(V_i+V_{i+1}+VL_{i/i+1})/ST$, in which expression $V_i$ denotes the volume of the distribution/extraction system of the departing plate $P_i$;
$V_{i+1}$ denotes the volume of the distribution/extraction system of the arriving plate $P_{i+1}$;
$VL_{i/i+1}$ denotes the volume of the by-pass line between $P_i$ and $P_{i+1}$;
and ST denotes the switch time; and
the super-synchronicity being defined by the formula:

super-synchronicity(%)=100×[(real flow rate in by-pass line under consideration/synchronous flow rate)−1].

2. A method for adjusting the flushing flow rates per operational zone in a simulated moving bed process in accordance with claim 1, in which the coefficients a and b allowing the super-synchronicity S to be applied to the flushing flow rates on the by-pass lines to be determined are given by the formulae:

a in the range −5 to +5;
b=(1320/total number of beds in SMB unit).

3. A simulated moving bed separation process according to claim 1, which the feed is a mixture of C8 aromatic hydrocarbons.

4. A simulated moving bed separation process according to claim 1, in which the feed is a mixture of C8 aromatic hydrocarbons.

* * * * *

UNITED STATES PATENT AND TRADEMARK OFFICE
CERTIFICATE OF CORRECTION

| | | |
|---|---|---|
| PATENT NO. | : 8,123,952 B2 | Page 1 of 1 |
| APPLICATION NO. | : 13/059773 | |
| DATED | : February 28, 2012 | |
| INVENTOR(S) | : Decoodt et al. | |

It is certified that error appears in the above-identified patent and that said Letters Patent is hereby corrected as shown below:

Column 14, Line 3 reads: "carbons." should read --carbons, and a para-xylene is separated--.

Column 14, Line 6 reads: "carbons." should read --carbons, and meta-xylene is separated--.

Signed and Sealed this
Eighth Day of May, 2012

David J. Kappos
*Director of the United States Patent and Trademark Office*